United States Patent [19]

Walker

[11] Patent Number: 5,326,538

[45] Date of Patent: Jul. 5, 1994

[54] CLOSED STERILIZATION SYSTEM FOR TREATING A PRODUCT SUCH AS TOXIC OR INFECTIOUS WASTE

[75] Inventor: David R. Walker, Clearwater, Fla.

[73] Assignee: Serawaste Systems Corporation, Tampa, Fla.

[21] Appl. No.: 669,449

[22] Filed: Mar. 13, 1991

[51] Int. Cl.⁵ .................................................. B09B 3/00
[52] U.S. Cl. .................................... 422/184; 422/296; 422/300; 34/242; 34/412; 277/15; 277/18; 277/59; 277/70
[58] Field of Search .............. 422/296, 300, 21, 184; 110/165 R, 165 A, 254, 255, 346; 431/165–167; 250/455.1; 198/657; 34/15, 242; 277/15, 18, 19, 27, 59–60, 70–71

[56] References Cited

U.S. PATENT DOCUMENTS

| | | |
|---|---|---|
| 779,625 | 1/1905 | Scheetz . |
| 1,539,333 | 5/1925 | Snyder . |
| 2,462,692 | 2/1949 | Vickers . |
| 2,486,939 | 11/1949 | Freund ................... 277/71 |
| 3,347,604 | 10/1967 | Lavelle et al. ............ 277/71 |
| 3,375,014 | 3/1968 | Chubb et al. ............. 277/71 |
| 3,547,577 | 12/1970 | Lovercheck . |
| 3,556,355 | 1/1971 | Ruiz ...................... 222/368 |
| 3,616,747 | 11/1971 | Lapeyre .................. 198/657 |
| 3,703,970 | 11/1972 | Benson ................... 241/241 |
| 3,825,270 | 7/1974 | Paramonoff et al. ..... 277/71 X |
| 3,831,288 | 8/1974 | Stribling et al. ............ 34/1 |
| 3,884,162 | 5/1975 | Schuster ................. 110/8 R |
| 3,895,745 | 7/1975 | Hook ..................... 222/368 |
| 3,922,975 | 12/1975 | Reese ..................... 110/8 F |
| 3,985,086 | 10/1976 | De Tola .................. 110/8 P |
| 4,037,795 | 7/1977 | Fyfe ....................... 241/58 |
| 4,050,907 | 9/1977 | Brimhall .................. 48/111 |
| 4,145,007 | 3/1979 | Jetzer ..................... 241/24 |
| 4,150,795 | 4/1979 | Link ...................... 241/33 |
| 4,179,043 | 12/1979 | Fischer ................... 222/368 |
| 4,185,973 | 1/1980 | Tester ..................... 55/212 |
| 4,250,139 | 2/1981 | Luck et al. ............... 422/21 |
| 4,529,134 | 7/1985 | Williams ................. 241/30 |
| 4,615,867 | 10/1986 | Heckmann .............. 422/109 |
| 4,707,334 | 11/1987 | Gerhard .................. 422/28 |
| 4,925,116 | 5/1990 | Lundell .................. 241/236 |
| 5,054,405 | 10/1991 | Walker ................... 110/254 |
| 5,072,949 | 12/1991 | Lopperi et al. .......... 277/71 X |
| 5,084,250 | 1/1992 | Hall ...................... 422/292 |
| 5,090,338 | 2/1992 | Harada et al. ........... 110/165 A |

FOREIGN PATENT DOCUMENTS 271454A 4/1988 Fed. Rep. of Germany ........ 422/21

Primary Examiner—Robert J. Warden
Assistant Examiner—Krisanne M. Thornton
Attorney, Agent, or Firm—Foley & Lardner

[57] ABSTRACT

The present invention relates to a closed sterilization system including an infeed device for receiving the toxic product, first preparing means for rendering the toxic or infectious product suitable for sterilization, sterilization means for sterilizing the product, combustion means for incinerating the sterilized product, and conveying means for conveying the sterilized product from the sterilization means into the combustion means. The system further includes a first isolating means positioned between the first preparing means and the inlet of the sterilizing means for isolating the product in the sterilizing means from the product in the first preparing means. Second isolation means are also positioned between the outlet of the sterilizing means and the conveying means for isolating the sterilized product from the product in sterilizing means. The first and second isolation means include a housing having an inlet and an outlet, conveying means disposed within the housing for moving the product from the inlet to the outlet and for isolating the product being discharged from the outlet from the product being received in the inlet.

16 Claims, 12 Drawing Sheets

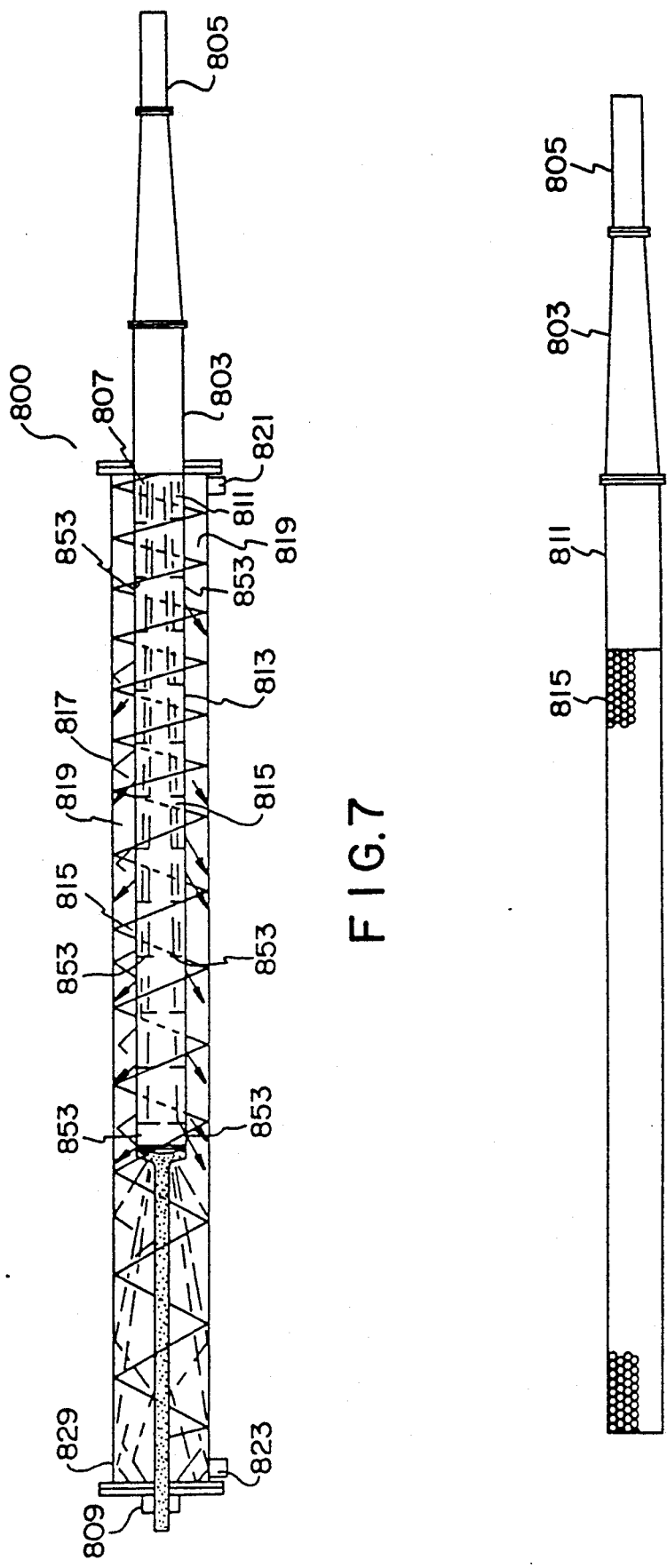

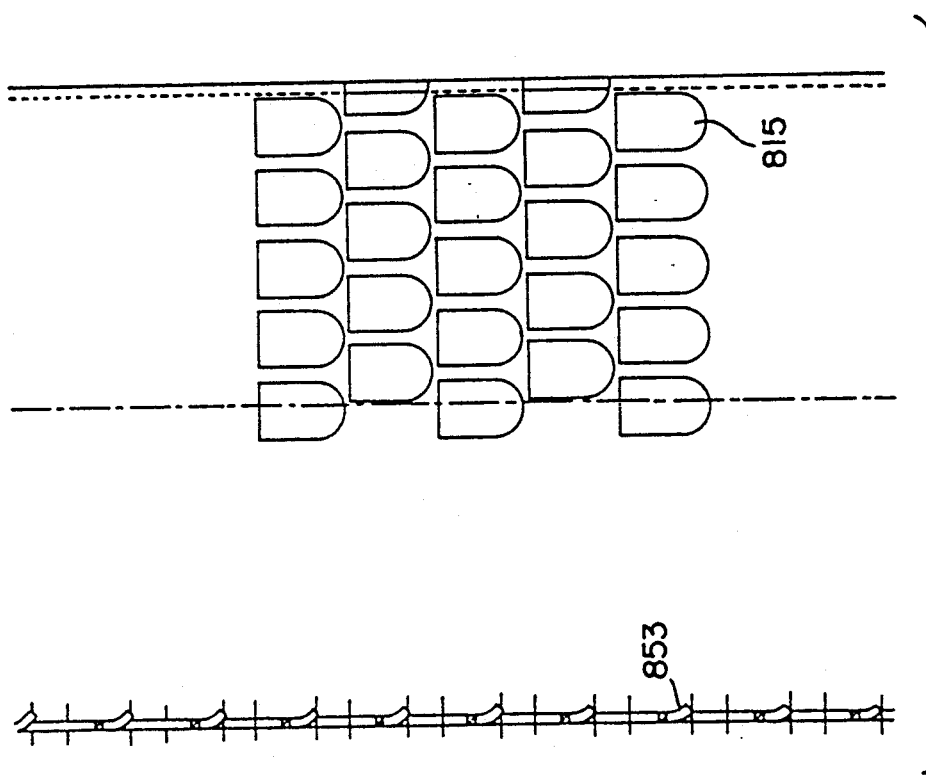

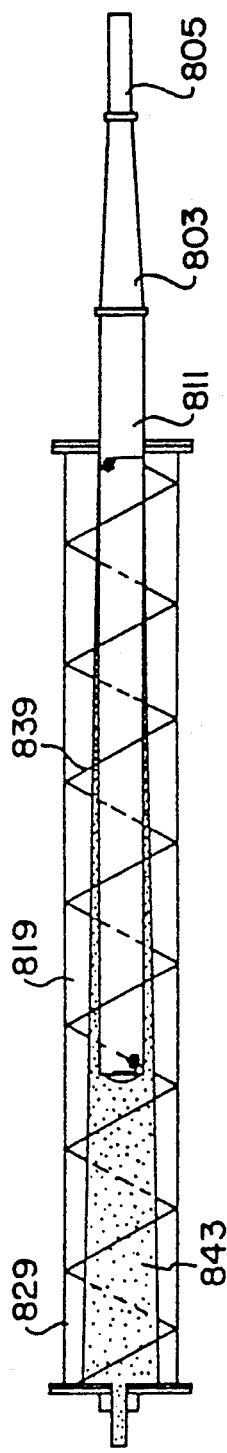
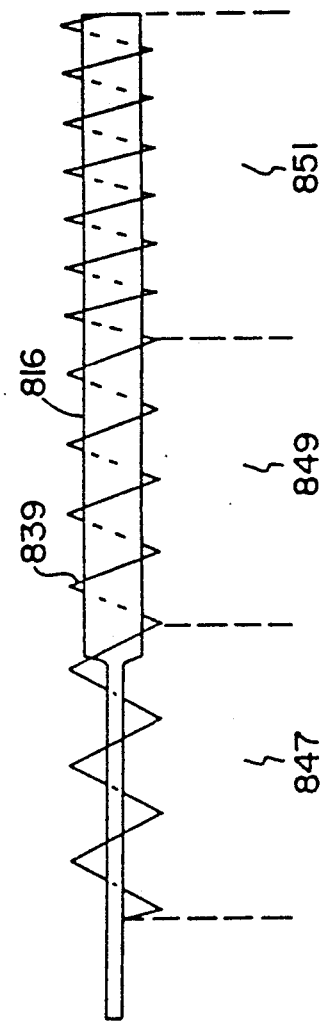
FIG.10
FIG.11

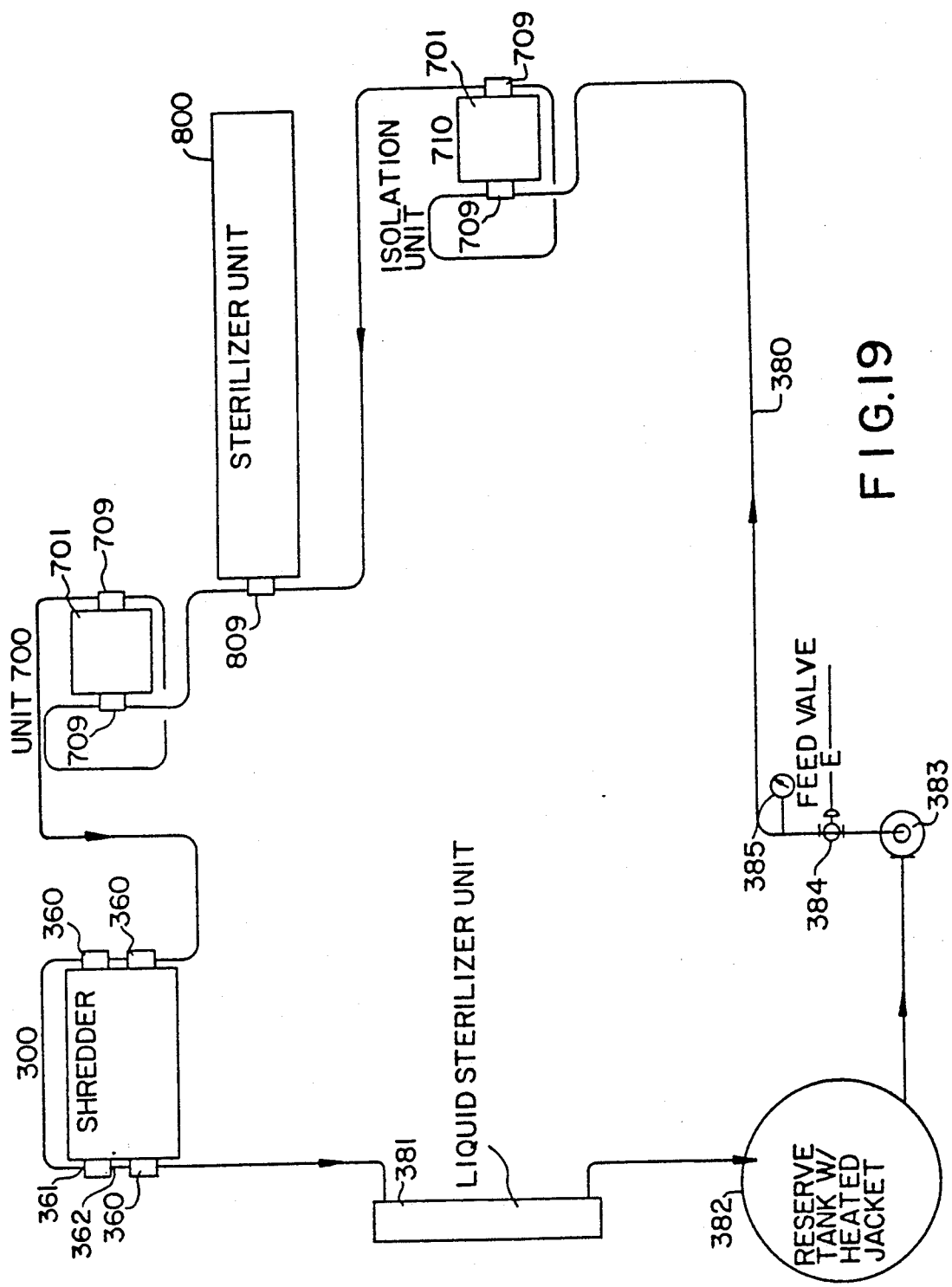

CLOSED STERILIZATION SYSTEM FOR TREATING A PRODUCT SUCH AS TOXIC OR INFECTIOUS WASTE

BACKGROUND OF THE INVENTION

The invention relates to a sterilization system, more particularly to a system for treating, sterilizing and burning a wide variety of toxic and infectious wastes within a completely closed system.

Health and environmental concerns have driven a search for sterilization and decontamination systems capable of efficiently sterilizing and destroying toxic waste without emitting the toxins into the outside environment. This is particularly true in the hospital environment where waste materials may carry highly infectious viruses such as the aids virus, which require the isolation, sterilization and incineration of these materials to avoid further contamination. Traditional sterilization systems which process and sterilize waste with a well known sterilizing medium such as germicidal sprays, tend to emit unacceptable amounts of toxins since the toxic waste is not effectively sealed within the treatment system and the sterilized waste is not prevented from commingling with the untreated waste. In addition, the burners normally located at the back end of the sterilizing medium tend to burn waste at relatively low temperatures thereby emitting unacceptably high levels of toxic fly ash and other pollutants.

Although some attempts have been made to sterilize thoroughly and incinerate toxic waste, these systems have proven ineffective in completely isolating and sterilizing the waste materials. For example, U.S. Pat. No. 4,185,973, which issued to Tester on Jan. 29, 1980, discloses a waste disposal system (eg. for a hospital), in which a series of shredders 2 pulverize the waste material. The pulverized waste is then drawn by air suction through a closed ducting system 53,54,56,58 for destruction. Each shredder has a discharge valve 66 positioned in the waste outlet which partly closes off the remainder of the system from the associated shredder when the waste input of the latter is open. This system while being an improvement over earlier systems by partially sealing the toxic waste from the sterile waste, is still deficient since it is arranged to provide incomplete sealing so that a small amount of air flows into the associated shredder. The shredder also has a vent opening in its waste inlet door to relieve pressure, as well as internal germicidal sprays. Furthermore, this system is not conducive to handling highly infectious waste material, since most germicidal sprays fail to sufficiently sterilize this type of highly toxic material thereby resulting in toxins being emitted in the environment during the combustion process.

U.S. Pat. No. 4,250,139 to Luck discloses a method for decontaminating proteinaceous host materials from microorganisms, while retaining the chemical, physical and physiological properties of the proteinaceous host materials. The method comprises dehydrating the host material and then subjecting it to lethal doses of microwave energy at ambient temperature. Although Luck discloses the broad concept of utilizing microwave energy as a more effective sterilizing medium, this system could not be used to treat toxic waste having a high moisture content since there are no provisions in this system for uniformly heating and treating waste material of varying moisture levels.

U.S. Pat. No. 4,037,795 issued to Fyfe discloses a centralized vacuum waste disposal system, particularly for use in hospitals. The system includes a shredder 10 which feeds into a remote incinerator via a ducting system 17,18,27. A set of air compressors 24,26 maintains a continuous upstream pressure substantially below atmospheric pressure to draw air carrying the pulverized waste through the ducting. To prevent contaminated air from escaping from the system if the compressor stops running, an auxiliary device is provided to maintain a partial vacuum at all times. This system lacks any highly efficient sterilizing medium.

U.S. Pat. No. 3,922,975 issued to Reese discloses a method and apparatus for feeding solid waste to a fluid bed disposal apparatus. The combustion assembly includes the waste delivery assembly 10 where solid waste material is collected, shredded and separated for introduction into the combustion assembly. In the combustion assembly 50, the solid waste is consumed and can also serve as a fuel to dispose of sludge. The combustion gas particle cleanup assembly 90 removes entrained particles from the combustion gases which are then either exhausted of conveyed on to perform work. An air lock feed valve 35 introduces the solid waste into a fluid conduit 36 where the material is pneumatically conveyed into the fluid bed.

This system, like the Fyfe system lacks any effective sterilizing medium for highly infectious waste or any isolator arrangement at the front and back end of the treatment step to ensure that the treated waste remains isolated from the untreated waste. Thus, the current art fails to disclose a closed sterilization system which economically and efficiently sterilizes toxic waste, while sealing the untreated toxic waste away from the treated waste.

SUMMARY OF THE INVENTION

It is therefore an object of the present invention to provide an economical and more efficient closed system for isolating and treating a wide variety of waste products, more particularly toxic and infectious waste products, such that the treated waste is always isolated from the untreated waste throughout the system and the incinerated waste is sterile and free from toxic fly ash.

It is a further object of the invention to provide a closed loop sealing subsystem for use with the closed sterilization system.

In achieving the stated objects, the present invention provides for a closed sterilization system including an infeed device for receiving the toxic product, first preparing means for rendering the toxic product suitable for sterilization, sterilization means for sterilizing the product, combustion means for incinerating the sterilized product, and conveying means for conveying the sterilized product from the sterilizing means into the combustion means.

The system further includes a first isolating means positioned between the first preparing means and the inlet of the sterilizing means for isolating the product in the sterilizing means from the product in the first preparing means. Second isolation means are also positioned between the outlet of the sterilizing means and the conveying means for isolating the sterilized product from the product in sterilizing means. The first and second isolation means include a housing having an inlet and an outlet, conveying means disposed within the housing for moving the product from the inlet to the outlet and for isolating the product being discharged from the outlet from the product being received in the inlet.

The conveying means of each isolating means includes a rotary shaft centrally disposed within the housing and having opposite ends protruding from the housing, at least two curved vanes rotatably mounted on the shaft and forming a compartment within a peripheral area of the housing between the inlet and outlet, the vanes rotating in a direction such that product is moved from the inlet to the outlet, with the inlet and outlet being longitudinally offset from each other relative to a centerline of the shaft, thereby ensuring that the product at the inlet is isolated from the product at the outlet. Seals surround each rotary shaft and abut the outer wall of the housing, each seal having chambers disposed therein with a longitudinally offset inlet and outlet for receiving and discharging a sterilant.

The infeed device may comprise a variable pitch infeed auger which creates a seal within the infeed by accelerating the infeed on the first part of the pitch, while slowing down the feed product by the variation of the pitch, thereby causing a plug at the outlet of the infeed, while the auger shaft remains at constant speed.

The first and second preparing means may comprise a shredder. The shredder includes a pair of parallel rotary shafts rotating in opposite directions, a plurality of discs or blades attached to each rotary shaft and having cutting surfaces for cutting and shredding the material, the discs being arranged on each shaft such that each pair of discs on opposite shafts matches each other sequentially at least once during one revolution of each rotary shaft, and drive means for driving the shaft to rotate. Seals similar in structure to the seals on the isolating means are also located proximate to each end of the rotary shafts for sealing and sterilizing each shaft of the shredder.

The sterilization means may comprise an inline electromagnetic wave applicator such as a microwave energy unit. This unit includes an inner chamber and a surrounding outer chamber separated at a distance from the inner chamber, the inner chamber having sides extending towards an interior of the chamber, the outer chamber having a product inlet and outlet and a conveyor for conveying the product from the inlet toward the outlet, a shaft extending into the inner chamber from the exterior sides of the outer chamber, and a microwave energy generation unit for transmitting microwave energy into an interior of the inner chamber, the microwave energy being diverted by the projections through the holes toward the outer chamber from radiating product in the outer chamber. A seal, similar in structure to the seals previously noted, surrounds the shaft and abuts the outer surface of the unit for sealing and sterilizing this portion of the shaft with respect to the housing. Of course, other seal configurations may be utilized which accomplish sealing and sterilizing the shaft with respect to the housing.

The combustion means includes a high temperature combustion device which meets or exceeds all applicable regulatory standards relating to the disposal of infectious or toxic waste. Since the product entering the burner is combusted at a very high temperature, this serves to ensure further that the residual ash of the burners is non-toxic and is therefore suitable for burying.

According to another aspect of the invention, the system has a distinct infeed and preparing means for handling non-toxic waste.

According to yet another aspect of the present invention, a closed-loop sealing - and sterilizing subsystem is provided for handling contaminated and infectious materials. This sealing system includes a plurality of devices each having a rotary shaft disposed therein, with at least one end protruding from the respective device, a seal surrounding each shaft and abutting the outside surface of each device, the seal having chambers disposed therein with an inlet and outlet offset from each other in relation to the shaft for receiving and discharging a sterilant. The sealing system further includes conduit means for transporting the sterilant through each seal such that the fluid circulates through and sterilizes the shaft of each device in the sterilization or other treatment system.

Other objects, features and advantages of the present invention will become apparent from the following detailed description. It should be understood, however, that the detailed description and the specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 7 is an elevation view, shown partially in cross section of an in-line microwave sterilization unit used in a preferred embodiment of the present invention.

FIG. 8 is a plan view of the microwave sterilization unit of FIG. 7.

FIG. 9 illustrates a spiral pattern of holes to provide a spiral pattern of energy wave diverters in the microwave sterilization unit.

FIG. 10 illustrates a compression shaft sterilizer of an embodiment of the microwave unit.

FIG. 11 is a plan view shown partially in cross section, of a variable pitch screw or helix conveyor suitable for use in the infeed of the system or the microwave sterilizer.

FIG. 19 is a schematic layout of a closed loop sealing sub-system used in a preferred embodiment of the present invention.

DETAILED DESCRIPTION OF THE PREFERRED EMBODIMENTS

A closed sterilization system according to the present invention, is designed to sterilize and burn infectious or toxic waste, particularly infectious hospital waste. This system is also capable of handling non-infectious waste which is primarily used as a fuel source for the burner. A broad range of materials may be handled by the system, including bones of varying hardness and size, plastic material of varying hardness and elasticity, soft body tissues, and fibrous materials manufactured from cotton or plastics.

The primary components of a system within the present invention include an infeed device for introducing material into the system, a shredder or other device to prepare the waste product for sterilization, a distinct infeed device and shredder to handle non-infectious waste, a sterilizing medium to sterilize the waste, a burner to incinerate the sterilized product, and a conveyor to convey the product from the sterilizer to the burner. Air lock valves are positioned between the shredder and the inlet of the sterilizer and the outlet of the sterilizer and the conveyor for isolating the sterilized product from the untreated product. A closed loop seal system also sterilizes each shaft of the various components of the sterilization system. Since the product entering the burner is combusted at a very high temperature, this serves to ensure further that the residual ash of the burners is non-toxic and is therefore suitable for burying. Thus, all toxic and infectious waste products remain in the closed system until they have been fully sterilized with residual toxins being removed during combustion.

Figure 1:
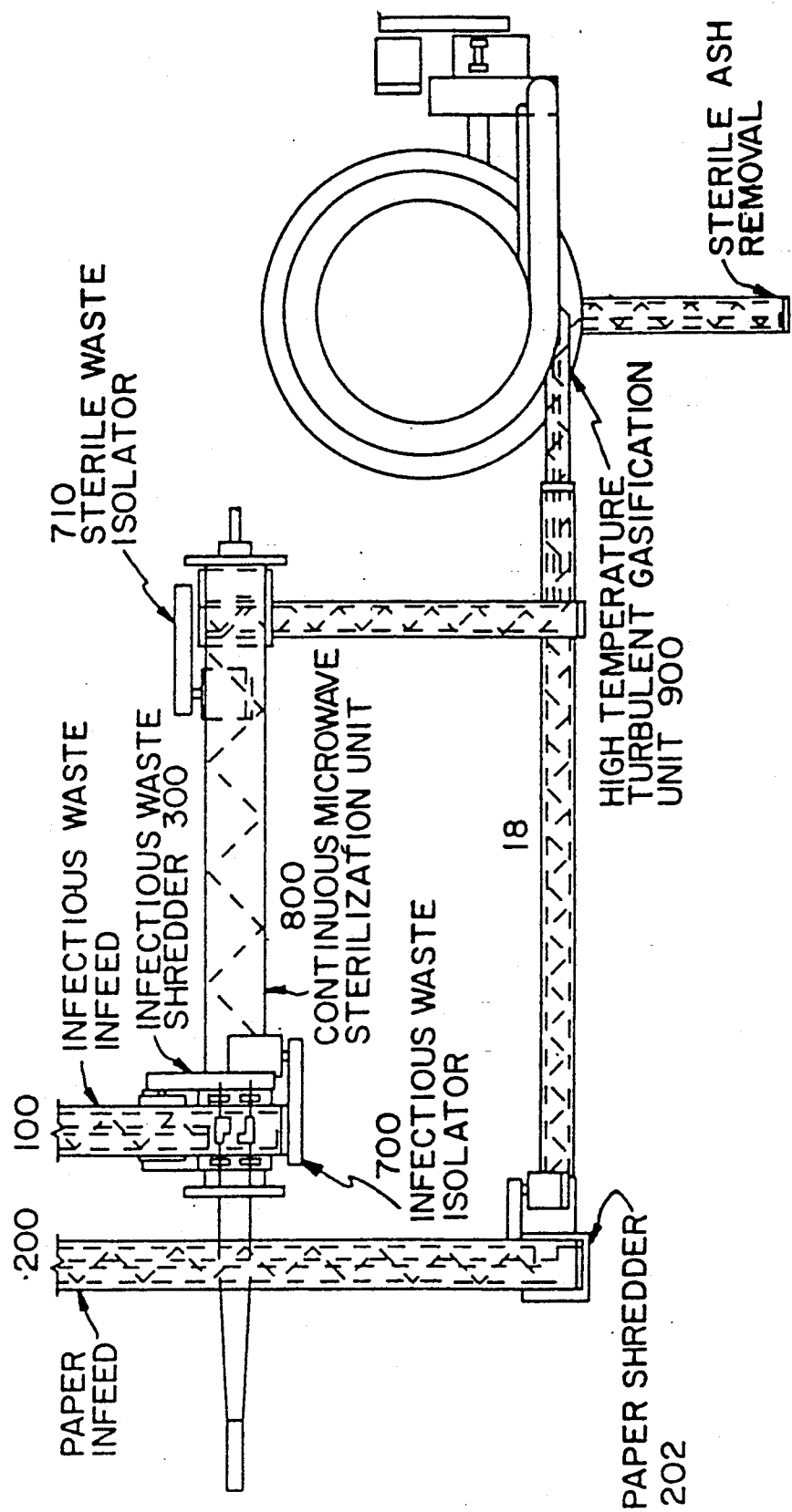
FIG. 1 is a plan view of the closed sterilization system of a preferred embodiment of the present invention.
Figure 2:
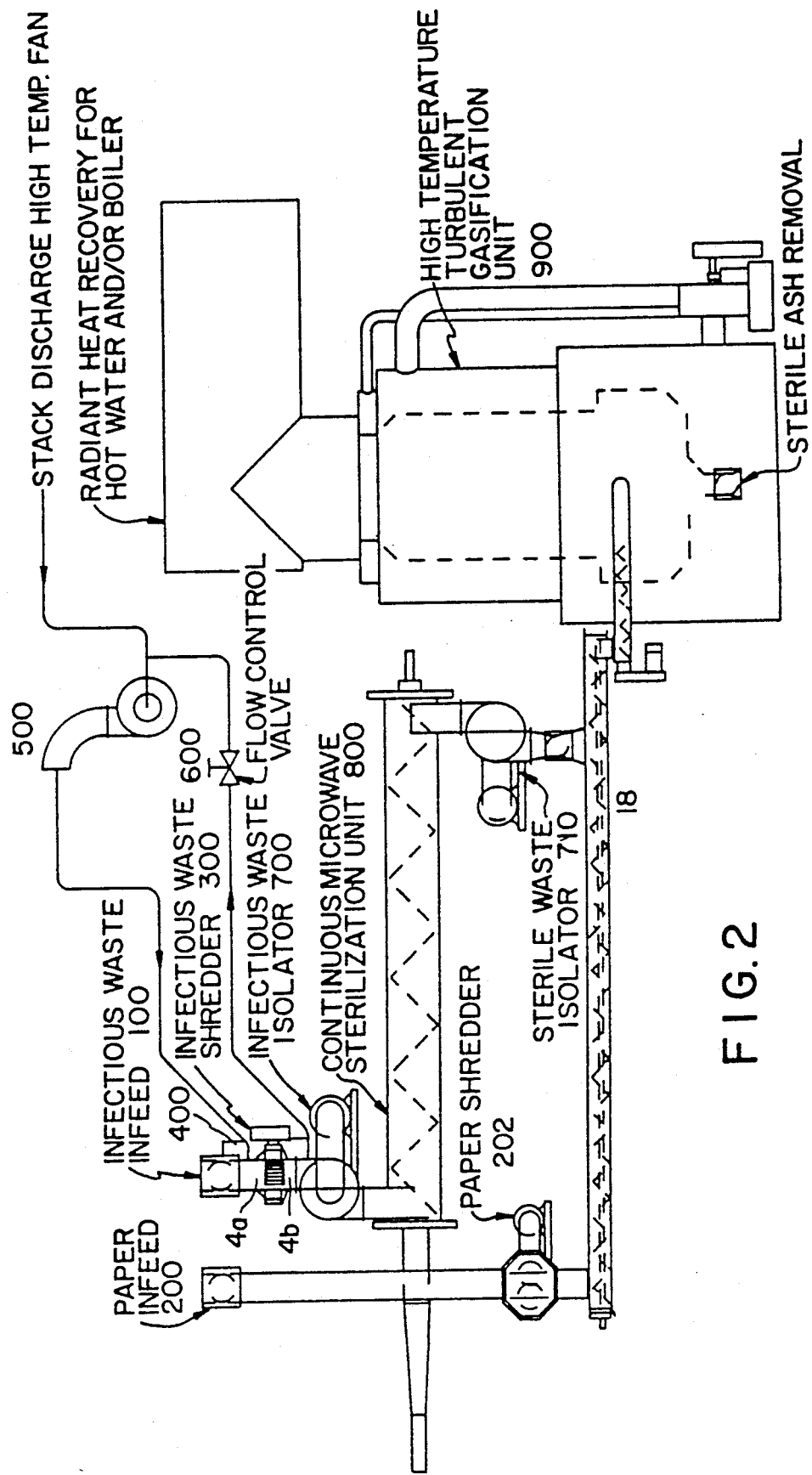
FIG. 2 is an elevation view of the closed sterilization system of a preferred embodiment of the present invention.

FIGS. 1 and 2 provide an overall layout of a treatment system in a preferred embodiment. As illustrated in FIGS. 1 and 2, infectious product enters the system at infeed 100. Infeed device 100 comprises a screw or other device to carry the material into the shredder 300. Non-infectious product enters the system at a separate infeed 200. Infeed device 200 comprises a screw or other means to transport the non-infectious product into a shredder 202.

To achieve an optimal power level and operating efficiency in the sterilizer, the infectious product must be shredded or otherwise prepared to ensure a steady stream of product which is uniform in size and consistency. The shredded product is then passed through a suitable infectious waste isolation unit 700, which prevents any contact of sterile with non-sterile product, thereby preventing contamination of the sterile product. The infectious product is then sterilized in the sterilization unit 800, which preferably uses microwaves as the sterilization medium. The sterilized product is then conveyed through a second isolation unit 710, which is identical in structure to unit 700, and thence into the burner or gassification unit 900, where the product is burned at high temperatures. A more detailed description of each component of the system will now be given below.

Figure 3:
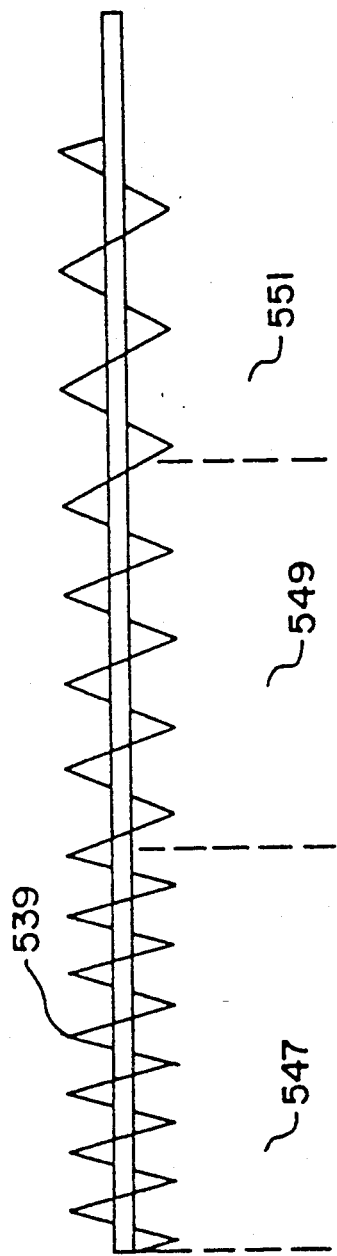
FIG. 3 is a perspective view of an infeed device of a preferred embodiment of the present invention.

The infeed device 100 preferably comprises a variable pitch auger which varies from full pitch to three quarter pitch to half pitch, depending upon the load flow of product. The auger serves the dual purpose of feeding the product into the shredder 300, as well as compressing the material so that it serves as a seal or plug to keep the air circulating through the shredder within the closed system. The variable pitch auger creates a seal by accelerating the product on the first part of the pitch, while slowing down the product by varying the pitch as the product flows through the auger, thereby causing a plug at the discharge of the auger or inlet of the first preparing means 300. Throughout the infeed of product the auger shaft operates at a constant speed. FIG. 3 illustrates a preferred variable pitch auger. As shown in FIG. 3, the helical conveyor 539 has a full pitch section 547, a ¾ pitch section 549 and a ½ pitch section 551. These sections or segments in the pitch of the conveyor allow for variations in the product flow through the infeed and into the shredder 300. As illustrated in FIG. 3, in the half pitch section 551 the number of turns is twice that of the full pitch segment 547. Thus, despite fluctuations of flow rate of material at the inlet, the variable pitch arrangement ensures that the material is effectively compressed and forms a seal at the discharge of the auger.

The infectious waste shredder 300 is preferably a high speed chopper which shreds the waste into pieces which are small enough to be sterilized and burned. The high speed chopper includes its own seal and ventilation system which allows for a completely closed operating system for the shredder. The air to operate the shredder is obtained from the gases discharged from the combustion device. This air is approximately 450°–800° F. and contains little or no moisture. The air is deemed inert because the effective combustion temperature and efficient air to fuel combustion in the furnace, leaves very little oxygen remaining in the discharged gas. The air to operate the shredder is preferably inert and at a preheated or higher temperature since this allows for a more efficient flow of product through the shredder and prevents condensation which could increase the moisture content of the product. Furthermore to enhance the closed nature of the shredding operation, as noted previously, the infeed auger compresses the material in a manner which creates a self-forming seal at the infeed portion of the shredder. A fan 500 is positioned between the exhaust of the furnace and the shredder for circulating the air and product through the shredder. The rate of circulation of the hot inert gas through the shredder is controlled by a feed rate valve, or pressure differential air valve 600 which is positioned between the discharge of the shredder and the fan 500. With this arrangement, the feed rate of air and product through the shredder is controlled. The area or chamber 4a, located between the discharge of the infeed screw and the shredder inlet, serves as the inert air chamber for the high speed shredder air flow. More specifically, Fan 500 pumps inert air from the furnace discharge into this chamber, thereby ensuring proper operation and a consistent feed rate into the shredder. The product is fed through the shredder in combination with the air. At the discharge of the shredder is a second area or chamber 4b, at which the air is discharged via the suction system of fan 500.

As evidenced above, the fan system 500 comprises a dual suction system. The first suction system is generated from the furnace discharge, and the second from the discharge chamber of the shredder. The suction is controlled by the valve 600, which compensates for any change in air suction or discharge pressure in each chamber. This method ensures that the system operates under a slight negative pressure, thereby sealing the inert gas within the system and preventing any infectious air or product from escaping into the outside environment.

Figure 4:
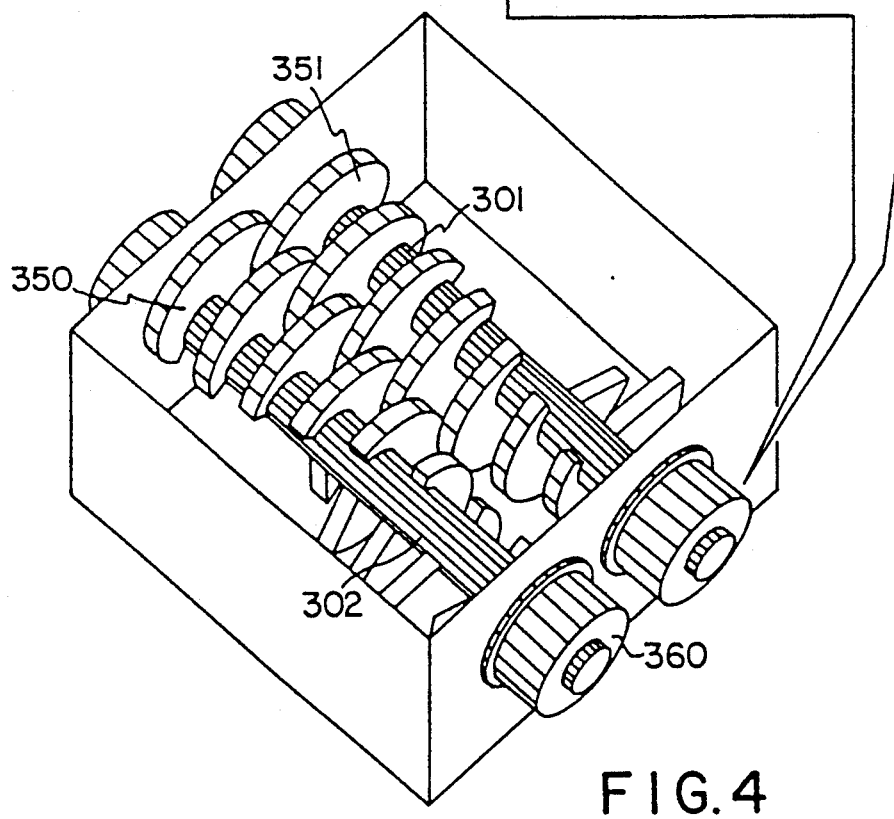
FIG. 4 is a perspective view of a shredder used in a preferred embodiment of the present invention.
Figure 5:
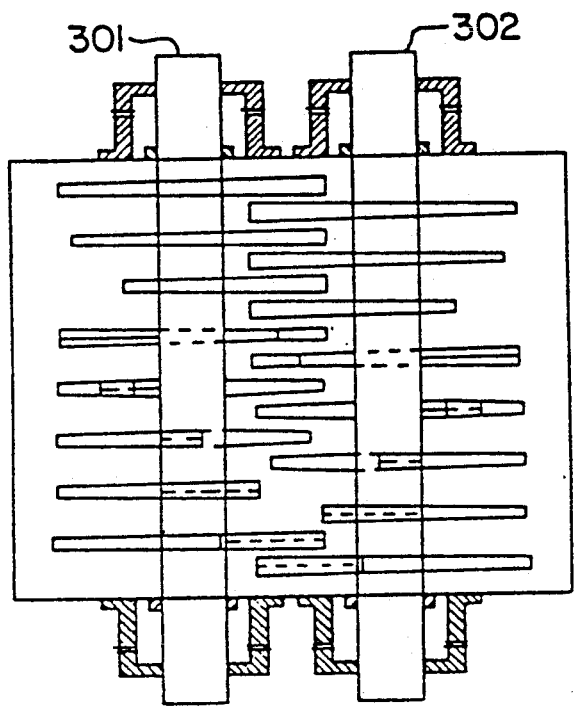
FIG. 5 is a plan and side view of the shredder of FIG. 4.
Figure 6:
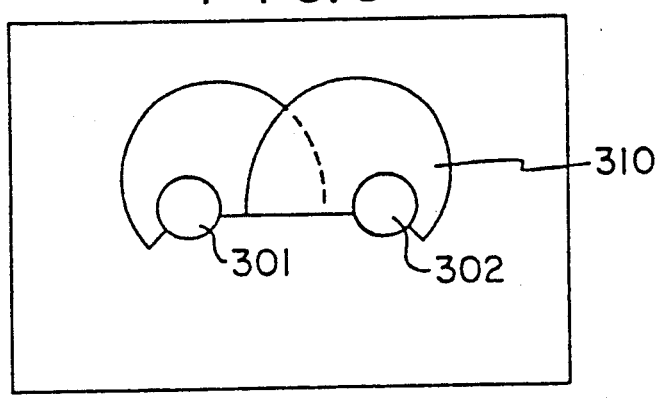
FIG. 6 is an end view of the shredder illustrated in FIG. 4.

FIGS. 4-6 depict the high speed shredder 300 of a preferred embodiment. Although this shredder is preferred, other conventional shredding or preparing devices may be used in its place. The preferred shredder is designed to uniformly shred material which is normally difficult to shred because of its hardness or its fibrous nature. As seen in FIGS. 4 and 5, shredder 300 consists of a pair of opposed rotary shafts 301 and 302 having a plurality of discs or blades 310 affixed thereon. As illustrated in FIGS. 5 and 6, the disc are configured in the well known "Archimedes Spiral" which tapers from the cutting surface of the disc rearward. This spiraling of the discs allows for an opening and closing effect of the discs, thereby allowing for easier handling of products which are bulky in nature, since a wider feed opening is provided between the blades. In this configuration, the shearface 350,351 of each disc is hardened to increase wear resistance and extends vertically from the shaft contact point to the outer radius of the disc or blade. The discs are tapered along their radial lengths to prevent "bridging" or clogging of the material within the shredder. For example, in a preferred design, the shearface of each disc extends from 1.5 inches back from the vertical surface along the entire height of the blade. As seen in FIG. 5, the thickness of the disc 310 is gradually reduced along the back of the outer radius of the disc to a thickness of one half of the shearface thickness at the tail of the blade. This arrangement ensures the continuous shredding of material by eliminating the likelihood of material jamming or bridging between the blades while the shredder is in operation.

Each disc is mounted on the shaft so that the vertical shearface is offset from the centerline of the shaft towards the direction of rotation of the shaft. This allows the force of impact during shredding to be transferred along a greater radius of the disc/shaft contact surface. As seen in FIGS. 4 and 6, the discs are mounted on the shafts so that the initial point of contact of two facing disc is below a tangent line formed by the mating shear faces of the disc. This ensures a uniform feed of material into the shredder and forces the material into position for contact with the next disc or blade. As illustrated in FIGS. 4 and 5, the blades are also arranged on the shaft so that each pair of blade faces match each other sequentially once during each revolution of the shafts. More specifically, the right-most blades match at the beginning of a revolution of the shafts, then the remaining sets of blades meet during subsequent portions of the cycle until the left-most blades meet at the end of the cycle. This sequential action in combination with the tapered nature of the blades produces an uneven and undulating surface during operation of the shredder, which creates a uniform distribution of material throughout the shredder and loosens parts of material that may be stuck together when they enter the shredder.

Figure 15:
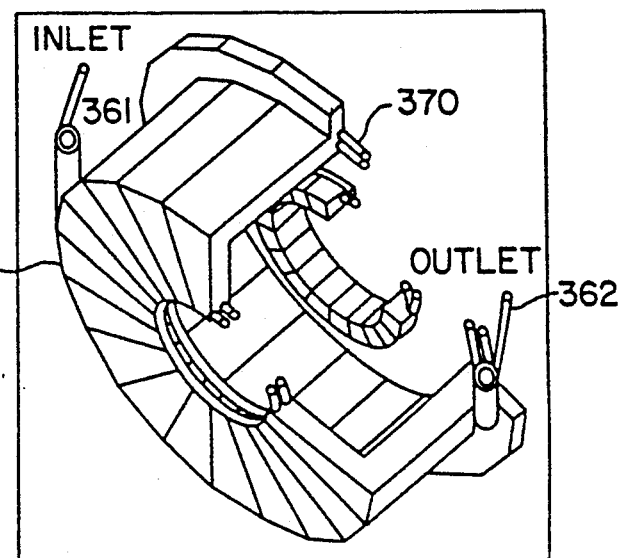
FIG. 15 is a perspective view of a shaft seal in a preferred embodiment of the present invention.

As shown in FIG. 15, surrounding each shaft of the shredder and abutting the shredder and the exterior of the housing of the shredder, are seals 360 which surround each shaft and serve the dual purpose of sealing and sterilizing the shaft with respect to the housing. Each seal is part of the closed-loop sealing and sterilizing subsystem which will be described in greater detail below. Of course, other seal configurations may be utilized which accomplish the sealing and sterilization of the shaft with respect to the housing.

Once the infectious material has been shredded or prepared, it is ready for sterilization. A variety of conventional sterilizing mediums may be used in the system such as chemical or steam units. Because of ever increasing energy cost and the desire to maximize efficiency, it is preferable to use microwave energy as the sterilizing medium. Microwave sterilization is also well suited to product having a varying moisture content, since these units provide more uniform heating and sterilizing of such product prior to combustion, thereby preventing infectious discharge during combustion of the sterilized product. Many type of microwave units can accomplish the sterilizing function.

A preferred embodiment of the present invention utilizes an in-line microwave applicator having an electromagnetic energy generation unit for transmitting energy waves along a longitudinal axis. Exemplary of this type of microwave unit is the in-line electromagnetic wave applicator described in pending U.S. patent application Ser. No. 07/625,666.

FIGS. 7-11 illustrate an in-line microwave sterilizer of a preferred embodiment. As seen in FIG. 7, the microwave unit 800 includes a microwave generation unit 805. Microwaves 807 are transmitted through transition section or transition coupling 803 to inner chamber 811. Inner chamber 811 has a surrounding wall 813 with a plurality of holes 815. Walls 813 are surrounded by a second set of walls 817 which, with walls 813 form a second or outer chamber 819. Outer chamber 819 also has product inlet 821 on the side nearest the microwave generator 805 and an outlet 823 on an opposite end. In order to divert microwaves 807 from inner chamber 811 to the outer chamber 819, a plurality of protrusions 853 are located along an interior portion of walls 813 of inner chamber 811.

As the microwaves in the inner chamber are interrupted and diverted by protrusions 853, they are transmitted through holes 815 into outer chamber 819. Infectious material passing from inlet 821 to outlet 823 through outer chamber 819 is radiated by the microwaves passing through the holes. Microwaves which are not absorbed by the material are reflected off the inner surface of the outer chamber to be absorbed by the material on a reflected path. Microwaves which are not absorbed at this stage are again reflected off the outside of walls 813 of inner chamber 811. As a result, material passing through the outer chamber is efficiently radiated and heated. In order to prevent product in the outer chamber 819 from falling into the inner chamber 811, the holes can be sealed with an external sleeve 816 made from material which is substantially transparent to microwaves. One such material is teflon. Alternatively, the entire outer wall 813 of inner chamber 811 can be surrounded by the sleeve. For example, the inner tube applicator assembly can be inserted directly into the cavity inside the sleeve. In addition, a screw type conveyor which is inside the outer chamber, as discussed below, can incorporate the sleeve into which the applicator is inserted.

The length of the outer chamber is longer than the length of the inner chamber. As is further discussed below, this allows further application of microwaves to product in the distal section 829 of the heating unit furthest from the microwave energy generating unit 805.

FIG. 8 shows a top view of the microwave applicator which is formed by microwave energy generating unit 805, transition coupling 803 and inner chamber 811. The electromagnetic waves typically have wave lengths of between 0.3 cm and 30 cm, corresponding to frequencies of 1 GHz to 100 Ghz. For sterilizing infectious wastes, the generator could be constructed to generate as much as 100,000 Watts of usable output energy.

As shown in FIGS. 7 and 8, a portion of inner chamber 811 has holes 815 which are formed in lines substantially parallel to each other with adjacent lines of holes being offset. As shown in FIG. 7, protrusions 853 extend from holes 815 into the interior portion of the inner chamber to form microwave diverters. The use of protrusions as microwave diverter is particularly useful when a very even heating of the material in the chamber is required with a minimum of hot spots.

The extension of the protrusions 853 into the inner chamber 811 becomes increasingly larger as the distance from microwave energy generating unit 805 increases. The protrusions 853 can be individual pieces connected to the inner chamber walls. Preferably, however, the protrusions 853 are formed by punching the holes into the walls of the inner chamber and using the punched lip to form the protrusion. Each punched hole in the line would have an increased size protrusion or lip 853 protruding into the flow of the wavelength, so as to direct the wavelength out of the slot at each contact with the punched lip. The wavelength is then directed into the material in the outer chamber, and, if not absorbed, hits the side wall of the outer chamber and then bounces back toward the product. With multiple waves, this procedure sets up a crossing of wavelengths bouncing against the chamber wall and the applicator metal, thus increasing the exposure to the material to be sterilized.

Hole size is a function of energy required for the heating application, such as sterilization. For instance, if an electromagnetic energy wave-generating unit is used with a large power capability on the order of 100,000 Watts, and the material to be sterilized has a solid-to-liquid ratio between 12% and 15% and if a conveyor moves the material through the outer tube at 250 lbs/hr, then the holes are sized to be ¾ inch by 1 ¼ inch. For applications in which the flow rate or the solid-to liquid-ratio is different, the required size of each hole changes proportionally, according to a linear relationship. For example, an applicator with a 50,000 Watt power source and hole sizes whose area is 50% that above for the 100,000 Watt power source would accommodate loads of 125 lbs/hr.

In heating applications requiring especially even heating, better distribution of the microwaves can be obtained by arranging the protrusions according to a spiral pattern. The spiral pattern is arranged to be clockwise or counter clockwise to correspond to the spiral pattern of screw type product conveyors which move the material to be heated through the outer chamber as discussed below. Such a spiral pattern of protrusions can be established by offsetting the centerline in a horizontal plane of each row of holes by five to ten degrees from the centerline of the adjacent row as illustrated in FIG. 9. Eventually, the centerline of a row matches the centerline of a first row. The spiral pattern of protrusions along with the increasing size of each protrusion as the distance from the microwave generator increases work together with the spiral screw shaped conveyors to establish greater distribution of electromagnetic energy to the product passing through the outer chamber Solids and semi-solid materials require a conveyor means to traverse the outer chamber 819. Screw type conveyors can be constructed of microwave transparent material, such as teflon, to avoid affecting the microwave paths in the outer chamber.

FIG. 10 illustrates a compression shaft heating unit with a full pitch helical coil for conveying the materials. In the compressive shaft, the material bed depth at the discharge end is forced to be narrower than the material bed depth at the in-feed end. This is because of the increasing thickness of shaft 843 in the outer chamber 819. As FIG. 10 shows, the distance between the walls of inner chamber 811 and outer chamber 819 is greatest at the in-feed end nearest the microwave energy generation unit 805 and narrowest at the end of the outer tube furthest from the microwave energy generation unit 805. As a result, the bed depth of the material is greater at the in-feed end than at the discharge end. This type of unit is useful for materials with low moisture content and which may be very infectious. The compression end maximizes the exposure to the wave pattern on the discharge end by decreasing the product bed depth. In addition, this configuration allows for a large volumetric feed and maximizes the in-feed rate.

FIG. 11 illustrates a variable pitch helical conveyor. One example is shown in Figure 11, in which the helical conveyor 839 has a full pitch section 847, a ¾ pitch section 849 and a ½ pitch section 851. These sections or segments in the pitch of the conveyor allow for variations in the product flow through the outer chamber. As shown in FIG. 7, in the half pitch section 851 the number of turns is twice that of the full pitch section 847. As material moves from the half pitch segment toward the full pitch segment of the helical conveyor coil, it slows down and the holding time in the second chamber during which the product is irradiated with electromagnetic energy waves is increased. As a result, the heating and sterilization efficiency of the material is improved. In some cases, this may also allow for operating the system at lower power levels.

Surrounding the shaft and attached to the exterior side of the outer chamber, is a seal 809 which surrounds the shaft and serves the dual purpose of sealing and sterilizing the shaft. This seal is identical in structure to the seals 360 illustrated in FIG. 15 and is part of the separate closed loop sealing and sterilizing subsystem which will later be described in greater detail. Of course, other seal configurations may be utilized which accomplish the sealing and sterilization of the shaft with respect to the housing.

Figure 12:
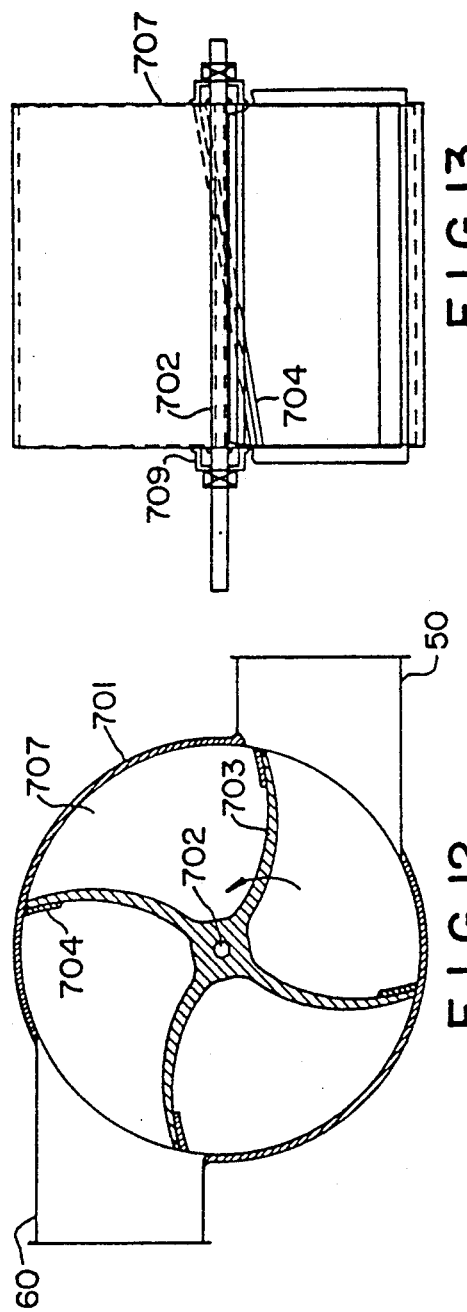
FIG. 12 is an end view of an air lock valve used in a preferred embodiment of the present invention.

As shown in FIGS. 1 and 2, a waste isolating unit 700 is positioned between the shredder and the inlet of the sterilizer for isolating the untreated shredded product from the product which is being sterilized in the sterilization medium. Similarly, a waste isolating unit 710 is located between the outlet of the sterilizer and the conveyor 18 for isolating the sterilized product from the untreated product in the sterilizer. In a preferred embodiment of the present invention, isolating Units 700 and 710 are air lock valves illustrated in FIGS. 12-14. As shown in FIG. 12, each air lock valve is designed to ensure that material at inlet 50 is never in contact with material at outlet 60. As seen in FIG. 12, the air lock valve includes a cylindrical drum 701 having a centrally positioned rotary shaft 702 which extends through opposite sides of the cylindrical drum. Vanes 703 are mounted on the rotary shaft such that they are in contact with the inside of the drum 701. The vanes are curved, each having a concave and a convex surface. A blade 704 is attached to the leading edge of each vane on the concave surface. The blades are provided on the leading edge of the vane to cut any fibrous material that would otherwise be caught in the vanes. The vanes rotate around the shaft 702 in a direction such that material is moved from the inlet 50 to the outlet 60. The number of vanes 703 is selected such that a completely enclosed compartment 707 will always be defined in a peripheral area of the drum between the inlet 50 and the outlet 60 which are offset from one another. Preferably, the compartment has a distance from the inlet of the sterilizer to the outlet of the air lock valve of no more than 25% of the internal circumferential distance of the air lock valve, i.e., no more than 25% of the internal circumferential distance of drum 701.

Figure 13:
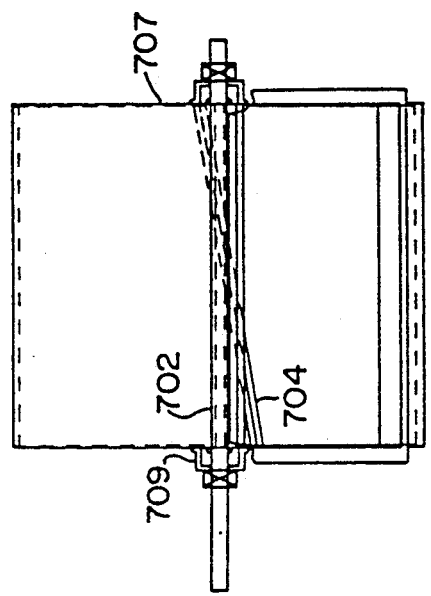
FIG. 13 is an elevation view partially in cross section of the air lock valve of FIG. 6.
Figure 14:
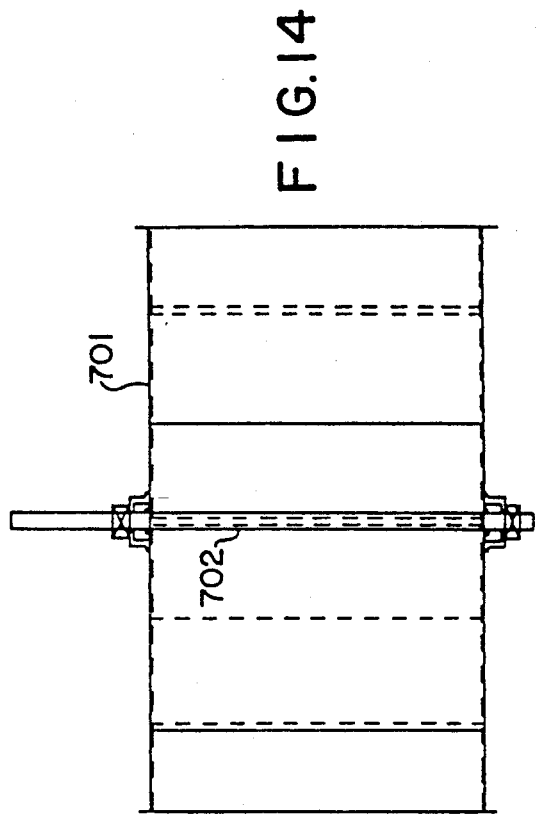
FIG. 14 is a plan view shown partially in cross section of the air lock valve of FIG. 6.

As shown in FIG. 13, proximate to each end of the shaft of the air lock valve are seals 709 which surround the shaft and serve the dual purpose of sealing and sterilizing the shaft. Each seal surrounds the through shaft and is attached to the housing of the air lock valve. This seal is identical in structure to seal 360 illustrated in FIG. 15, and is also part of the closed-loop sealing and sterilization subsystem to be outlined below.

The closed-loop sealing and sterilization subsystem is designed to sterilize all the outboard shafts of the sterilization system to ensure that no infectious material leakage occurs outside each shaft. In this system a seal solution is pumped in a closed loop to all seals, then back through an inline high temperature liquid sterilizer. After the solution is sterilized it is recirculated through the seal system. The seals are also designed so that any failure will pump the sterilant back into the infectious product. Although this seal system is suitable for the present invention, its scope is not limited to this particular design as it can be used with a wide variety of sterilization and other waste treatment systems.

FIGS. 15 and 19 illustrate a preferred embodiment of the sealing and sterilizing subsystem of the present invention. As seen in FIG. 15 which illustrates the seals for the shredder, each seal includes a housing 365 surrounding a shaft, e.g., 301 in FIG. 3, and is attached to the exterior of the housing of the associated device in the system, eg. the shredder 300. The seal housing has chambers 370 disposed therein. The chambers have an inlet 361 and outlet 362 for receiving the sterilant. Although shown schematically in FIG. 19 as being longitudinally centered on the housing, the inlet 361 and outlet 362 are preferably longitudinally offset from one another as shown in FIG. 15 to increase the flushing effect or turbulence of the sterilant within the housing, thereby enhancing sterilizing efficiency. The sterilant can be any sterilizing fluid such as iodine, which is pumped in the chamber via inlet 361, where it flushes and cleans the shaft before exiting the chamber via outlet 362.

The schematic of the entire closed-loop system is clearly illustrated in FIG. 19. A conduit system 380 interconnects the seals of each device with the fluid sterilizer unit 381, the reserve tank 382, and the pump 383. Initially, sterilant is supplied to the pump 383 from the reserve tank 382. The sterilant is then pumped through the conduit network 380 first through the seals 709 of isolation unit 710, then through the seal 809 on the exterior shaft of the sterilizer. The sterilant is then pumped through the seals 709 of isolating unit 700, back-through the seals 360,360 of the output and input shafts of the shredder, and finally through the liquid sterilizer unit 381, where the sterilant is sterilized before reentering the reserve tank via the same conduit network. A feed valve 384 and pressure gauge 385 are positioned proximate the pump 383 to control the level of sterilant that is circulated through the system. As seen in FIG. 19, the sterilant flows through each seal in reverse order of product flow to keep the sterilant at its maximum effectiveness by passing it through the more sterile product first, thereby allowing maximum utilization of sterilant before it must be reheated or replaced. Of course, other seal subsystems may be utilized which accomplish the sealing and sterilizing of the shafts of each device with respect to their corresponding housings.

After the material is sterilized and leaves the sterile waste isolator 710, it enters conveyor 18 where it meets with the non-infectious shredded product and is conveyed into the combustion unit 900 where the waste material is burned at high temperatures. Exemplary of high-temperature burners which can be used in this regard is high-temperature gassification unit described in U.S. patent application Ser. No. 07/607,118, now U.S. Pat. No. 5,054,405 the contents of which are hereby incorporated by reference. But the objectives of this invention can be effected with other types of high-temperature combustion units, and the gasification unit illustrated in detail below is a preferred component only.

Figure 16:
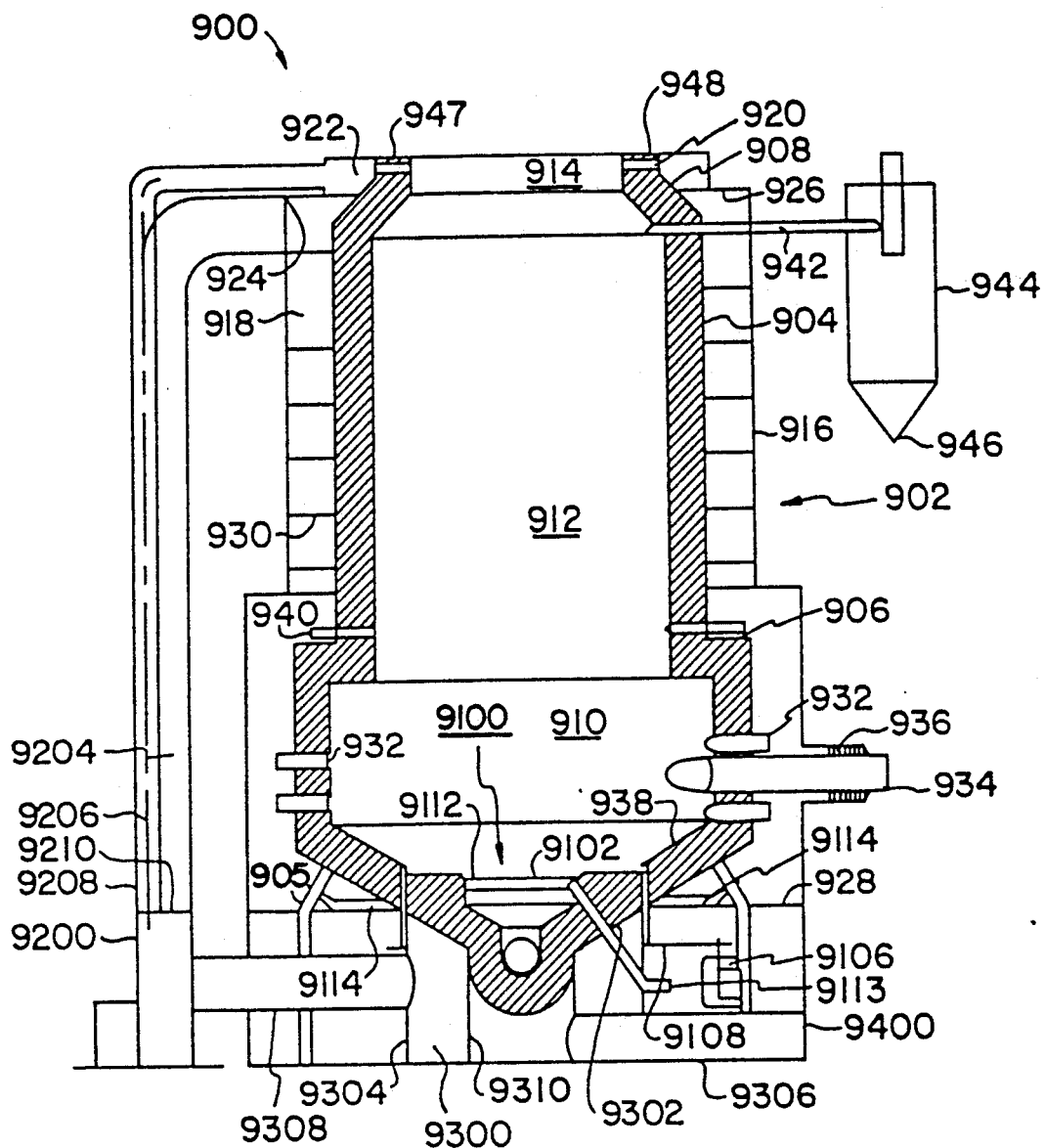
FIG. 16 is a schematic representation, shown partially in cross section, of a side view of a gasification unit used in a preferred embodiment of the present invention.
Figure 17:
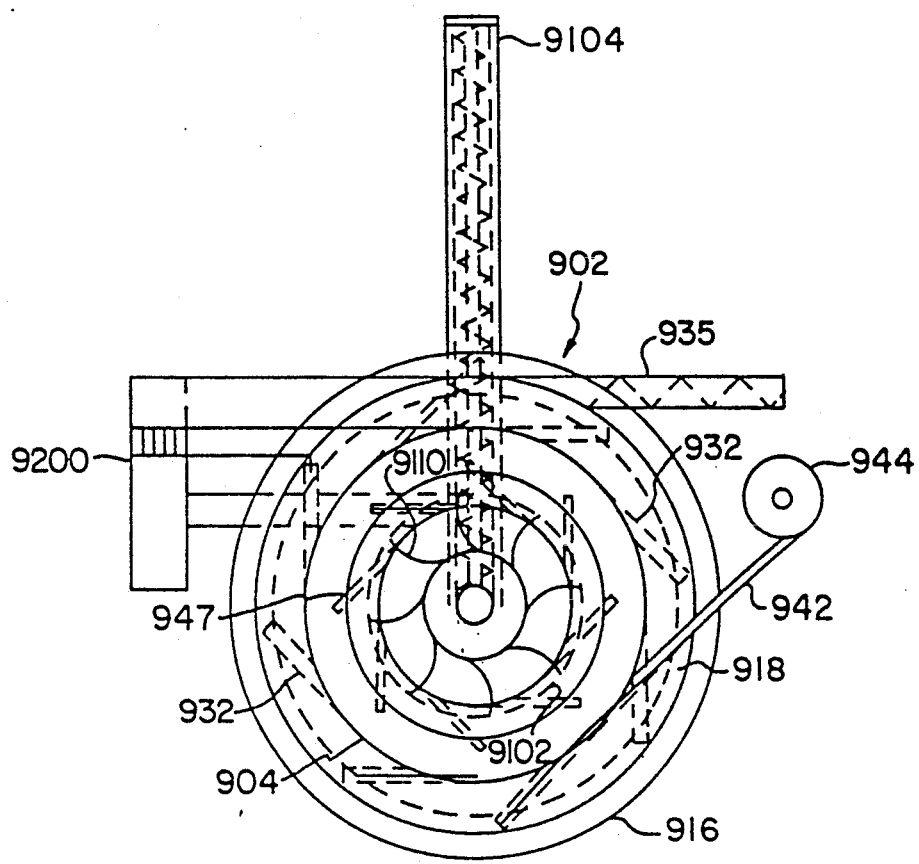
FIG. 17 is a schematic representation of a top view of the gasification unit illustrated in FIG. 16.
Figure 18:
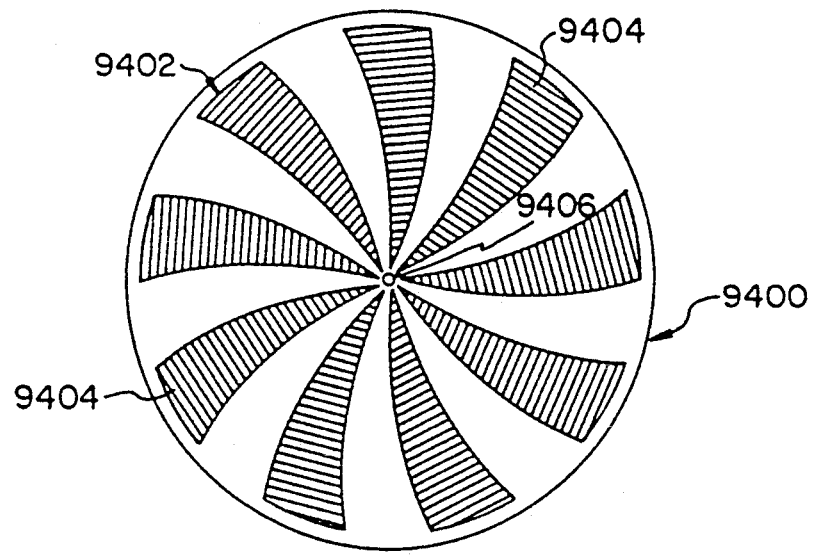
FIG. 18 is a front view of a shutter device used in the gasification unit of FIG. 16.

With reference to FIGS. 16–18, a furnace 900 includes a generally cylindrical refractory liner 904. The refractory liner 904 is mounted on supports 905 and includes a first step 906 which defines a boundary between a primary combustion chamber 910 and a secondary combustion chamber 912. Refractory liner 904 further includes a second step 908 which defines a boundary between the secondary combustion chamber 912 and a tertiary combustion chamber 914. A first generally cylindrical shell 916 surrounds a portion of refractory liner 904 to define a preheating chamber 918 for primary and secondary combustion air, and a second shell 920 defines an inlet chamber 922 for tertiary combustion air. An apparatus 9100 is positioned in the bottom of refractory 904 for sterilizing and removing residual ashes from the bottom of a primary combustion chamber 910. A fan 9200 has an inlet connected to a cooling chamber 9300 and an outlet connected to preheating chamber 918 and to tertiary air inlet chamber 922.

Cooling chamber 9300 surrounds a lower portion 9302 of the refractory liner 904 and has a generally cylindrical outer wall 9304 separating the chamber from the ambient atmosphere. Cooling chamber 9300 includes an inlet which cooperates with the ambient atmosphere via an inlet conduit 9306 and an outlet which is connected to an inlet of fan assembly 9200 via an outlet conduit 9308. The inlet and outlet conduits 9306 and 9308 are vertically offset from one another to increase the turbulence of air within the chamber 9300. Vertical baffles 9310 extend part-way across chamber 9300 on opposite sides of the chamber to force air flowing through the chamber to circulate around refractory liner portion 9302.

A manually operated shutter device 9400 controls the airflow rate into the inlet conduit 9306 and generates a spiral airflow within the conduit that increases turbulence within the cooling chamber 9300 to increase the heat transfer efficiency within the cooling chamber. This device, illustrated in greater detail in FIG. 18, comprises a pair of circular plates 9402 mounted in the inlet conduit. These plates are superimposed one in front of the other so that only one of these plates can be seen when the device is in the fully open position illustrated in FIG. 18. Each of these plates comprises a plurality of generally spiral-shaped vanes 9404 mounted on a central shaft 9406. The outer plate is fixed on the shaft, and the inner plate is adapted to rotate about the shaft, and is driven manually via a handle (not shown).

When the inner plate 9402 is rotated to the position illustrated in FIG. 17 so that the vanes 9404 of the respective plates 9402 are superimposed one in front of the other, air may be drawn into the inlet conduit between the spaces formed between the vanes 9404. The curved surfaces of these vanes cause air flowing through the device to rotate in a generally spiral pattern. The airflow rate through the device can be decreased simply by rotating the inner plate so that the vanes of the respective plates are no longer superimposed, thereby reducing the effective spacings between the vanes. When the inner plate is rotated so that its vanes completely block the openings formed between the vanes of the outer plate, airflow through the shutter is essentially blocked.

After entering the inlet conduit 9306 through the shutter device 9400, combustion air is drawn through cooling chamber 9300 where it circulates around refractory liner portion 9302 in contact therewith before exiting the cooling chamber. The flow of air past the refractory liner heats the combustion air, for example, to a temperature of about 200°-250° F. and cools the refractory liner. This cooling effect allows the provision of a refractory liner which is considerably thinner than conventional liners, thereby lowering the cost and size of the unit.

After exiting the cooling chamber 9300 via conduit 9308, the combustion air is drawn through fan 9200 and is then forced through first and second conduits 9204 and 9206 and into preheating chamber 18 and tertiary air inlet chamber 920. Shutter devices 9208 and 9210 control the flow rate of combustion air through conduits 9204 and 9206. These shutter devices are identical in construction to shutter device 9400 but are operated automatically in a manner which is known-per se. The control devices for these shutters typically comprise a control system which monitors temperatures and combustion efficiencies within the primary, secondary, and tertiary combustion chambers and which actuate pneumatically-controlled valves to vary the opening degrees of the shutters. The combustion efficiencies may be sensed, e.g., by monitoring at least one of the oxygen, carbon, and hydrocarbon levels within the combustion chambers.

From conduit 9204, combustion air flows through an inlet 924 extending tangentially into preheating chamber 918 and thence into the preheating chamber in a generally spiral pattern. The generally cylindrical preheating chamber is bordered on the top and bottom by walls 926 and 928 and at the outside by shell 916. The fan 9200 is oversized to supply air into chamber 918 at a sufficiently high pressure to force the air down into chamber 918, thereby pressurizing the preheating chamber.

While flowing towards the primary and secondary combustion air ports, the combustion air present within the preheating chamber 918 is preheated to a temperature of 250°-350° F. via contact with the outer surface of refractory liner 904, with the amount of preheating depending on the length of time for which the air remains in the preheating chamber. By preheating the combustion air in this manner, the combustion efficiency of the unit is greatly enhanced without requiring the provision of separately fueled burners to preheat the air.

In order to increase the retention time of air in the preheating chamber and hence the temperature of the combustion air at the inlet ports for the combustion chambers, baffles 930 are provided in the preheating chamber 918. Although they are not absolutely essential, these baffles prevent combustion air from "short circuiting" by travelling vertically from the inlet 924 to inlet ports for the combustion chambers 910 and 912. The number and placement of these baffles can be varied to meet the combustion requirements of the particular material being incinerated.

Combustion air flowing into the portion of preheating chamber 918 surrounding primary combustion chamber 910 enters the primary combustion chamber via inlet ports 932 extending through the side wall of the refractory liner 904. As illustrated in FIG. 17, these ports extend tangentially through the side wall of the refractory liner 904 and into the primary combustion chamber in a direction which is opposite to the direction of the substantially spiral flow of combustion air. By orientating the inlets in this manner, the unit ensures that the direction of the airflow must be reversed before it enters the combustion chamber. This reversal of airflow not only increases the pressure of air flowing into the combustion chamber, but also ensures that the pressure will be equalized at all inlet ports. This results in increased turbulence within the primary combustion chamber, which in turn results in increased combustion efficiency. The tangential introduction of combustion air into the primary combustion chamber further increases the turbulence in the chamber. As illustrated in FIGS. 16 and 17, the pipes or other members forming inlet ports 932 actually extend into the preheating chamber 918 by a sufficient amount to prevent the formation of eddy currents within the preheating chamber, which eddy currents tend to decrease the flow rate of combustion air into the combustion chamber. These ports are designed to supply the amount of oxygen required for maximum combustion efficiency within the primary combustion chamber. Although they are illustrated as being positioned literally tangential to the wall of the refractory liner, these inlet ports may be angled by as much as 8 degrees from the wall of the refractory liner without substantially affecting the operation of the ports.

Sterilized product is injected into primary combustion chamber 910 via product inlet 934 located between rows of combustion air inlets 932. This inlet, like the combustion air inlet ports, extends tangentially through the side wall of the refractory liner to increase turbulence within the chamber. In addition, the product is injected at relatively high speeds via a high-speed conveyor 935, a fan, or some other suitable conveying device. This high speed tangential injection breaks up larger clumps of materials and promotes maximum mixing of the materials with the combustion air, thereby increasing combustion efficiency within the primary combustion chamber. In a preferred embodiment, the injection device is provided with air inlets 936 which cooperate with the preheating chamber 918. These inlets draw preheated combustion air into the product to heat the product within the injection device to a temperature of at least 212° F. This heating increases combustion efficiency by allowing moisture within the materials to boil away immediately upon the injection of materials into the primary combustion chamber.

A sloped portion 938 of the refractory liner 904 defines a portion of the floor of the primary combustion chamber 910. The angle of the slope is set to increase the air turbulence adjacent the slope and to maximize the retention time of the product within the combustion chamber in contact with the combustion air. The angle of this slope is dictated by the density and particle size of the material being incinerated and the ash content of the material. The slope can be increased or decreased in dependence on the density and percentage of ash, with denser ashes having a greater tendency to accumulate, thereby requiring a greater slope.

As discussed above, the refractory liner 904 includes a step 906, located at the top of the primary combustion chamber 910, which defines the bottom of the secondary combustion chamber 912. This step increases the radial airflow around the top of the primary combustion chamber to increase further the turbulence within the primary combustion chamber and to form a barrier at the top of the chamber which suppresses the emission of materials from the primary combustion chamber.

The suppression effect of the step 906 is supplemented by the injection of secondary combustion air into the secondary combustion chamber via inlet ports 940. These ports, like primary combustion air inlet ports 932, extend tangentially through the side wall of refractory liner 904 to ensure a radial flow of pressurized air in the secondary chamber. This radial flow of air accelerates the flow of materials within the chamber, thereby further to suppress material flow out of the primary combustion chamber 910. The secondary inlet ports differ from the primary inlet ports only in that they are narrower to ensure an optimum air/fuel mix within the secondary combustion chamber. Those unburnt materials which penetrate the suppression layer and travel into the secondary chamber are thus intensely mixed with the secondary combustion air and are incinerated.

The step 908 defining the bottom of the tertiary combustion chamber 914 creates a second suppression area at the top of secondary combustion chamber 912. This suppression area once again increases the airflow velocity around the combustion chamber, thereby increasing the retention period of materials within the secondary combustion chamber and reducing fly ash emissions. In addition, this acceleration increases further the turbulence within the secondary combustion chamber to increase further the combustion efficiency. The radial flow of materials around the suppression area of the secondary combustion chamber also centrifically forces fly ash to the outside of the chamber where it is removed to a separation tank 944 via a conduit 942. The conduit 942 extends tangentially through the side wall of the refractory liner and is directed parallel to the direction of airflow within the secondary combustion chamber in order to facilitate flow of fly ash into the conduit. Fly ash entering the separation tank 944 settles to the bottom of the tank where it is removed via a valve 946, which is designed to allow the ash to flow out of the tank while minimizing heat losses. The opening degree of the valve will depend on the volume and density of ash removed from the unit.

Combustion products exiting the top of secondary combustion chamber 912 enter tertiary combustion chamber 914, where they are mixed with combustion air entering the chamber tangentially from tertiary inlet chamber 920 and tertiary inlet ports 947. Top and bottom ends of the chambers are defined by a wall 948 and by the wall 926 defining the top wall of the preheating chamber 918. Although the structure and operation of the tertiary inlet ports is essentially identical to that of the primary and secondary inlet ports, the pressure of the air is separately controlled via the shutter 9208 located in conduit 9206. These tertiary inlet ports not only provide for additional combustion of any remaining product, but also allow the unit to control the temperatures within the chamber by increasing or decreasing the flow rate of relatively cool tertiary air. This tertiary combustion air can thus be used to cool the materials exiting the unit to a desirable level for further manipulations, such as afterburning or releasing the exhausts directly to the atmosphere. In the absence of such further manipulations, this tertiary air would be used as the gas for fan 500 which circulates this gas through the shredder 300.

Ashes remaining in the bottom of primary combustion chamber 910 are sterilized and then removed from the unit via apparatus 9100. Apparatus 9100 includes a powdered ash removal device 9102 which is rotatably mounted on the floor of the unit and which conveys the residual ashes from the bottom of sloped wall 938 of the refractory to a centrally located outlet leading to a conveyor 9104, which in turn transports the ashes away from the unit. The ash removal device is driven via a variable speed motor 9106 and a conventional chain or belt drive mechanism 9108. Device 9102 is also provided with spiral blades 9110 which are constructed from a cast material and which transport the ashes to the central outlet of the unit. The rotary speed of the device 9102 is set so that the blades 9110 gently break up any remaining clumps of materials and roll the material over without stirring it, thereby exposing any unburnt materials to oxygen for incineration while minimizing the production of fly ash. The retention time of the residual ashes in the removal device is determined by the shape of the blades 9110 and by the speed of rotation of the device. In a preferred embodiment, the device is designed to maintain the residual ashes in the device for at least 5 seconds.

In order to ensure sterilization of the residual ashes within the burner, the apparatus 9100 includes a plurality of second stage burner nozzles 9112 which are positioned beneath the device 9102 and which heat the materials in the device to a uniform temperature of at least 1800° F. The burners are fed by a conduit 9113 connected to a source of fuel in a conventional manner. These burners also function as a continuous pilot for the primary combustion chamber 910 by igniting materials which are injected into the chamber.

A cooling system is also provided in the apparatus 9100 to prevent warping of the cast blades 9110 and to keep powdered ashes out of the drive system for the ash removal device. This cooling system includes conduits 9114 which extend through a wall of preheating chamber 918 to allow preheated air to flow to the ash removal device 9102. Preheated air is preferred for this operation because ambient air would produce an undesirably high temperature differential across the device 9102, which temperature differential could damage the device or decrease the efficiency of the sterilization process. The chamber into which the cooling air flows is sealed with a gasket material (not shown) which is capable of withstanding the high temperatures present in this chamber. This gasket material prevents cooling air from entering the primary combustion chamber.

By incinerating completely waste materials and by sterilizing residual ashes, the gassification unit described above meets or exceeds all applicable regulatory standards relating to the disposal of hospital wastes. Thus, these gasification units are especially well-suited to incinerate infectious or contaminated waste products typically produced by hospitals. However, as noted above, other high temperature incineration devices can be used without destroying the scope and spirit of the present invention.

What is claimed is:

1. A sterilization system for treating a product comprising:
   (A) first infeed means for feeding a product into said system;
   (B) first preparing means for receiving said product from said first infeed means and for rendering said product suitable for sterilization;
   (C) sterilizing means for sterilizing said product, said sterilizing means having an inlet for receiving said product from said first preparing means and an outlet for discharging a sterilized product;
   (D) combustion means for incinerating said sterilized product;
   (E) first conveying means for conveying said sterilized product from said outlet of said sterilizing means into said combustion means;
   (F) first isolation means, positioned between said first preparing means and the inlet of said sterilizing means, for isolating product present in said sterilizing means from the product present in said first preparing means;
   (G) second isolation means, positioned between said outlet of said sterilizing means and said first conveying means, for isolating said sterilized product from the product in said sterilization means, wherein each of said first and second isolation means comprises
      (i) a housing having an inlet and an outlet and (ii) second conveying means, disposed within said housing, for moving said product from said housing inlet to said housing outlet and for isolating said product being discharged from said housing outlet from said product being received in said housing inlet;
   wherein said second conveying means comprises
      a rotary shaft centrally disposed within said housing and having opposite ends protruding from said housing;
      at least two curved vanes rotatably mounted on said shaft and forming a compartment within a peripheral area of said housing between said housing inlet and outlet, said vanes rotating in a direction such that product is moved from said housing inlet to said housing outlet;
   wherein said housing inlet and outlet are longitudinally offset from each other relative to a centerline of said shaft, thereby ensuring that said product being received in said housing inlet is isolated from said product being discharged from said housing outlet; and
   wherein each of said rotating vanes of said second conveying means has a curved cross section and a cutting edge at a tip thereof which contacts an inner surface of said housing, said cutting edge having a helical trace relative to an axis of rotation of the rotary shaft thereby enabling said rotary shaft to cut any product which may become caught on the edge of the vane.

2. A sterilization system as claimed in claim 1, wherein said first infeed means comprises a screw type auger.

3. A sterilization system as claimed in claim 1, wherein said second conveying means comprises electric drive means for varying the speed of said shaft.

4. A sterilization system as claimed in claim 1, wherein said rotating vanes together form a compartment having a circumferential distance of not more than 25% of the internal circumferential distance of said housing, and
   wherein the circumferential distance from a trailing edge of said housing inlet to a leading edge of said housing outlet is more than 25% of the internal circumferential distance of said housing.

5. A sterilization system for treating a product comprising:
   (A) first infeed means for feeding a product into said system;
   (B) first preparing means for receiving said product from said first infeed means and for rendering said product suitable for sterilization;
   (C) sterilizing means for sterilizing said product, said sterilizing means having an inlet for receiving said product from said first preparing means and an outlet for discharging a sterilized product;
   (D) combustion means for incinerating said sterilized product;
   (E) first conveying means for conveying said sterilized product from said outlet of said sterilizing means into said combustion means;
   (F) first isolation means, positioned between said first preparing means and the inlet of said sterilizing means, for isolating product present in said sterilizing means from the product present in said first preparing means;
   (G) second isolation means, positioned between said outlet of said sterilizing means and said first conveying means, for isolating said sterilized product from the product in said sterilization means, wherein each of said first and second isolation means comprises
      (i) a housing having an inlet and an outlet and (ii) second conveying means, disposed within said housing, for moving said product from said housing inlet to said housing outlet and for isolating said product being discharged from said housing outlet from said product being received in said housing inlet;
   wherein said second conveying means comprises
      a rotary shaft centrally disposed within said housing and having opposite ends protruding from said housing;
      at least two curved vanes rotatably mounted on said shaft and forming a compartment within a peripheral area of said housing between said housing inlet and outlet, said vanes rotating in a direction such that product is moved from said housing inlet to said housing outlet; and
   wherein said housing inlet and outlet are longitudinally offset from each other relative to a centerline of said shaft, thereby ensuring that said product being received in said housing inlet is isolated from said product being discharged from said housing outlet;

further comprising seals surrounding each end of said rotary shaft, abutting an outside wall of said housing, and including means for sealing and sterilizing each end of said rotary shaft, each of said seals having an inlet and an outlet longitudinally offset from each other in relation to said rotary shaft, and conduit means, extending from each of said inlets of said seals and said outlets of said seals, for receiving and discharging a sterilant.

6. A sterilization system as claimed in claim 1, further comprising
   (i) second infeed means, distinct from said first infeed means, for feeding a non-toxic product into the system; and
   (ii) second preparing means, distinct from said first preparing means, for receiving said non-toxic product from said second infeed means and rendering it suitable for incineration, said second preparing means including an inlet for receiving said non-toxic product and an outlet for discharging said non-toxic product into the first conveying means.

7. A sterilization system for treating a product comprising:
   (A) first infeed means for feeding a product into said system;
   (B) first preparing means for receiving said product from said first infeed means and for rendering said product suitable for sterilization;
   (C) sterilizing means for sterilizing said product, said sterilizing means having an inlet for receiving said product from said first preparing means and an outlet for discharging a sterilized product;
   (D) combustion means for incinerating said sterilized product;
   (E) first conveying means for conveying said sterilized product from said outlet of said sterilizing means into said combustion means;
   (F) first isolation means, positioned between said first preparing means and the inlet of said sterilizing means, for isolating product present in said sterilizing means from the product present in said first preparing means;
   (G) second isolation means, positioned between said outlet of said sterilizing means and said first conveying means, for isolating said sterilized product from the product in said sterilization means, wherein each of said first and second isolation means comprises
      (i) a housing having an inlet and an outlet and (ii) second conveying means, disposed within said housing, for moving said product from said housing inlet to said housing outlet and for isolating said product being discharged from said housing outlet from said product being received in said housing inlet;
   wherein said first preparing means is a shredder; and
   wherein said first preparing means further comprises a closed loop air device configured for eliminating a need for outside air within said shredder, thereby preventing gases within said shredder from discharging to the atmosphere.

8. A sterilization system as claimed in claim 7, wherein said closed loop air device comprises:
   a fan, having an outlet connected to an inlet of said shredder and an inlet connected to an outlet of said combustion means and to an outlet of said shredder.

9. A sterilization system for treating a product comprising:
   (A) first infeed means for feeding a product into said system;
   (B) first preparing means for receiving said product from said first infeed means and for rendering said product suitable for sterilization;
   (C) sterilizing means for sterilizing said product, said sterilizing means having an inlet for receiving said product from said first preparing means and an outlet for discharging a sterilized product;
   (D) combustion means for incinerating said sterilized product;
   (E) first conveying means for conveying said sterilized product from said outlet of said sterilizing means into said combustion means;
   (F) first isolation means, positioned between said first preparing means and the inlet of said sterilizing means, for isolating product present in said sterilizing means from the product present in said first preparing means;
   (G) second isolation means, positioned between said outlet of said sterilizing means and said first conveying means, for isolating said sterilized product from the product in said sterilization means, wherein each of said first and second isolation means comprises
      (i) a housing having an inlet and an outlet and (ii) second conveying means, disposed within said housing, for moving said product from said housing inlet to said housing outlet and for isolating said product being discharged from said housing outlet from said product being received in said housing inlet;
   wherein said first preparing means is a shredder comprising:
      a housing having an inlet and an outlet;
      a pair of parallel rotary shafts rotating in opposite directions;
      a plurality of discs or blades attached to each rotary shaft and having surfaces for shredding said product, said discs being arranged on each shaft such that each pair of discs on opposite shafts matches each other sequentially at least once during one revolution of each rotary shaft; and
      drive means for driving said shafts to rotate; and
   wherein said rotary shafts include sealing means, surrounding each shaft and abutting said housing of said shredder, for sealing and sterilizing each shaft.

10. A sterilization system as claimed in claim 9, wherein said discs of said shredder are configured in the shape of an Archimedes spiral which tapers from a cutting surface rearward and are mounted on the shafts so that an initial point of contact of two facing discs is below a tangent line formed by a mating of edges of said spiral.

11. A sterilization system as claimed in claim 9, wherein said sealing means comprises
   seals, each of said seals having an inlet and outlet longitudinally offset from each other in relation to said rotary shaft, and
   conduit means extending from said inlet and outlet of each seal for receiving and discharging a sterilant.

12. A sterilization system for treating a product comprising:

(A) first infeed means for feeding a product into said system;

(B) first preparing means for receiving said product from said first infeed means and for rendering said product suitable for sterilization;

(C) sterilizing means for sterilizing said product, said sterilizing means having an inlet for receiving said product from said first preparing means and an outlet for discharging a sterilized product;

(D) combustion means for incinerating said sterilized product;

(E) first conveying means for conveying said sterilized product from said outlet of said sterilizing means into said combustion means;

(F) first isolation means, positioned between said first preparing means and the inlet of said sterilizing means, for isolating product present in said sterilizing means from the product present in said first preparing means;

(G) second isolation means, positioned between said outlet of said sterilizing means and said first conveying means, for isolating said sterilized product from the product in said sterilization means, wherein each of said first and second isolation means comprises
   (i) a housing having an inlet and an outlet and (ii) second conveying means, disposed within said housing, for moving said product from said housing inlet to said housing outlet and for isolating said product being discharged from said housing outlet from said product being received in said housing inlet;

wherein said sterilizing means comprises a microwave energy sterilization unit; and wherein said microwave energy sterilization unit comprises:
   an inner chamber and a surrounding outer chamber separated at a distance form the inner chamber, the inner chamber having sides with a first plurality of holes, each hole having a projection extending towards an interior of the inner chamber, the outer chamber having a product inlet and a product outlet and a conveyor for conveying product form the product inlet toward the product outlet;
   a shaft extending into the inner chamber from an exterior side of the outer chamber; and
   a microwave energy generation unit for transmitting microwave energy into an interior of the inner chamber, the microwave energy being diverted by the projections through the holes toward the outer chamber for radiating product in the outer chamber.

13. A sterilization system as claimed in claim 12, wherein said conveyor comprises a generally spiral shaped screw type conveyor.

14. A sterilization system as claimed in claim 12, further comprising a seal surrounding the shaft proximate an exterior end of said shaft and abutting an outside surface of said microwave unit, said seal having an inlet and outlet longitudinally offset from each other in relation to said shaft, and wherein conduit means extend from said inlet and outlet of said seal for receiving and discharging a sterilant.

15. A sterilization system for treating a product comprising:

(A) first infeed means for feeding a product into said system;

(B) first preparing means for receiving said product from said first infeed means and for rendering said product suitable for sterilization;

(C) sterilizing means for sterilizing said product, said sterilizing means having an inlet for receiving said product from said first preparing means and an outlet for discharging a sterilized product;

(D) combustion means for incinerating said sterilized product;

(E) first conveying means for conveying said sterilized product from said outlet of said sterilizing means into said combustion means;

(F) first isolation means, positioned between said first preparing means and the inlet of said sterilizing means, for isolating product present in said sterilizing means from the product present in said first preparing means;

(G) second isolation means, positioned between said outlet of said sterilizing means and said first conveying means, for isolating said sterilized product from the product in said sterilization means, wherein each of said first and second isolation means comprises
   (i) a housing having an inlet and an outlet and (ii) second conveying means, disposed within said housing, for moving said product from said housing inlet to said housing outlet and for isolating said product being discharged from said housing outlet from said product being received in said housing inlet;

wherein said combustion means is a gasification furnace comprising:
   A) a refractory liner surrounding a primary combustion chamber;
   (B) means for drawing combustion air past a portion of said refractory liner in contact with an outer surface thereof such that said combustion air is preheated and said refractory liner is cooled;
   (C) means for injecting said combustion air into said primary combustion chamber via primary air inlets formed in said refractory liner;
   (D) means for injecting waste product into said combustion chamber via a product inlet formed in said refractory liner; and
   (E) means for sterilizing and then removing residual ashes from said gasification furnace.

16. A sterilization system as claimed in claim 10, wherein the discs on opposite shafts cooperate to produce an alternating opening and closing effect which alternately increases and decreases the width of a feed opening for said product, the length of which feed opening extends in a direction parallel to an axial direction of said rotary shafts.

* * * * *